United States Patent
Horvath et al.

(10) Patent No.: US 9,617,359 B2
(45) Date of Patent: Apr. 11, 2017

(54) PERFLOUORO-T-BUTOXY ALLYL AND PROPARGYL ETHERS

(71) Applicant: City University of Hong Kong, Kowloon, Hong Kong (HK)

(72) Inventors: Istvan T. Horvath, Hong Kong (CN); K. C. Lau, Hong Kong (CN); Matthew Y. Lui, Hong Kong (CN); Edwin Law, Hong Kong (CN); Kwun Chung Paul Wong, Hong Kong (CN)

(73) Assignee: City University of Hong Kong, Hong Kong (HK)

( * ) Notice: Subject to any disclaimer, the term of this patent is extended or adjusted under 35 U.S.C. 154(b) by 0 days.

(21) Appl. No.: 14/260,674

(22) Filed: Apr. 24, 2014

(65) Prior Publication Data

US 2014/0323672 A1     Oct. 30, 2014

Related U.S. Application Data

(60) Provisional application No. 61/816,432, filed on Apr. 26, 2013.

(51) Int. Cl.
| | |
|---|---|
| *C07C 43/17* | (2006.01) |
| *C08F 14/18* | (2006.01) |
| *C08F 38/00* | (2006.01) |
| *C08F 216/14* | (2006.01) |

(52) U.S. Cl.
CPC .......... *C08F 14/185* (2013.01); *C07C 43/17* (2013.01); *C08F 14/18* (2013.01); *C08F 38/00* (2013.01); *C08F 216/1408* (2013.01)

(58) Field of Classification Search
CPC ................................................. C07C 43/17
See application file for complete search history.

(56) References Cited

U.S. PATENT DOCUMENTS

| | | | |
|---|---|---|---|
| 3,541,159 A * | 11/1970 | Pittman ............... | C07C 43/123 568/684 |
| 4,029,867 A * | 6/1977 | Wasley ................. | C08F 8/00 526/247 |
| 5,886,115 A * | 3/1999 | Crivello ................ | C08F 4/26 526/126 |

FOREIGN PATENT DOCUMENTS

| | | | |
|---|---|---|---|
| FR | 2566401 A1 * | 12/1985 | ............ C07C 41/16 |
| GB | 1153187 A * | 5/1969 | ........... C07D 303/22 |

OTHER PUBLICATIONS

Dear et al., "Fluorinated Acetylenic Alcohols and Derived Allenes", Journal of Organic Chemistry, 1968, 33(2), 819-823.*
Trofimenko et al., "Perfluoroacetylenic Ethers", Journal of Organic Chemistry, 1978, 43(1), 43-47.*
Horváth, et al., Facile Catalyst Separation Without Water: Fluorous Biphase Hydroformylation of Olefins, Science, vol. 266, Oct. 7, 1994.
Herrera, et al., Tuning the fluorous partition coefficients of organometallic complexes. The synthesis and characterization of $[\eta^5\text{-}C_5H_4CH_2CH_2(CF_2)_9CF_3]Rh(CO)L$ (L=CO or $P[CH_2CH_2(CF_2)_5CF_3]_3$) and $Cl_2Ni\{P[CH_2CH_2(CF_2)_5CF_3]_3\}_2$, Inorganic Chemistry Communications 1, 1998, pp. 197-199.
Luebker, et al., Interactions of flurochemicals with rat liver fatty acid-binding protein, Toxicology, 176 (2002) pp. 175-185, www.elsevier.com/locate/toxicol.
Horváth, I. T., Changing Designer Issues in Fluorous Chemistry, Department of Chemical Technology and Environmental Chemistry, Eötvös University, Pázmány Péter sétány 1/A, Budapest, H-117 Hungary, International Symposium on Fluorous Technologies, p. 6, Jul. 3-6, 2005, Bordeaux/Talence, France.
Kudo, et al., Induction by perfluorinated fatty acids with different carbon chain length of peroxisomal β-oxidation in the liver of rats, Chemico-Biological Interactions, 124, 2000, pp. 119-132, www.elsevier.com/locate/chembiont.
Das, et al., Effects of Perfluorobutyrate Exposure during Pregnancy in the Mouse, Toxicological Sciences 105(1), 173-181 (2008), doi:10.1093/toxsci/kfn099, Advance publication May 28, 2008, published by Oxford University Press 2008.
Kiss, et al., An improved design of fluorophilic molecules: prediction of the in P fluorous partition coefficient, fluorophilicity, using 3D QSAR descriptors and neural networks, Journal of Fluorine Chemistry, 108 (2001), pp. 95-109, www.elsevier.com/locate/jfluchem.

* cited by examiner

*Primary Examiner* — Nicole M Buie-Hatcher
(74) *Attorney, Agent, or Firm* — Heslin Rothenberg Farley & Mesiti, P.C.; Philip Hansen

(57) ABSTRACT

Perfluoro-t-butoxyallyl ether and perfluoro-t-butoxypropargyl ether and methods for their synthesis are disclosed. Also disclosed are methods for making polymers from the perfluoro-t-butoxyallyl ether and perfluoro-t-butoxypropargyl ether.

5 Claims, No Drawings

PERFLOUORO-T-BUTOXY ALLYL AND PROPARGYL ETHERS

CROSS REFERENCE TO RELATED APPLICATIONS

This application claims priority from U.S. provisional application 61/816,432, filed Apr. 26, 2013, the entire contents of which are incorporated herein by reference.

FIELD OF THE INVENTION

The invention relates to the synthesis, characterization and use of perfluoro-t-butoxyallyl and propargyl ethers.

BACKGROUND

Perfluoro-t-butoxyallyl ether and perfluoro-t-butoxypropargyl ether are previously unknown in the chemical art. However, other allyl ethers and propargyl ethers are known, and their utility as monomers for incorporation into homo and copolymers having advantageous electrical, mechanical and thermal properties are known.

SUMMARY OF THE INVENTION

In a first aspect the invention relates to compounds of formula $(CF_3)_3COCH_2R$ wherein R is —CH=CH$_2$ or —C≡CH.

In a second aspect, the invention relates to polymers comprising repeating units of formula III or IV:

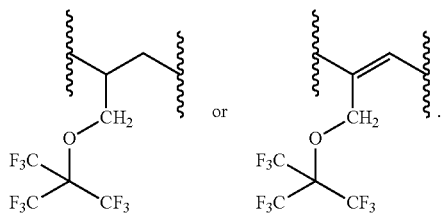

In a third aspect, the invention relates to a process for preparing a compound of formula I comprising reacting an allyl halide with either: (a) a salt of nonafluoro-tert-butoxide, or (b) nonafluoro-tert-butyl alcohol in the presence of a base.

In a fourth aspect, the invention relates to a process for preparing a compound of formula II comprising reacting a propargyl halide with either: (a) a salt of nonafluoro-tert-butoxide, or (b) nonafluoro-tert-butyl alcohol in the presence of a base.

DETAILED DESCRIPTION OF THE INVENTION

Substituents are generally defined when introduced and retain that definition throughout the specification and in all independent claims.

In a composition aspect, the invention relates to compounds of formulae I and II:

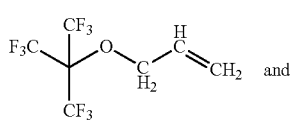 and

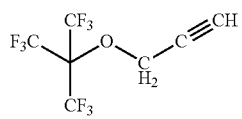

The compounds are synthesized as follows.

3-[1,1-bis(trifluoromethyl)-2,2,2-trifluoroethoxy]prop-1-ene (I) was prepared by adding 12.2 mL (141 mmol) allyl bromide to a stirred solution of 1.1 equivalent or 40.0 g (155 mmol) sodium nonafluoro-tert-butoxide in 40 mL N,N-dimethylformamide at room temperature and then by heating at 50° C. After 72 hours the addition of 20 mL water to the reaction mixture resulted in the formation of two liquid phases. The lower phase was separated, washed with 20 mL of 2M NaOH four times and with distilled water two times. The reaction mixture was purified by vacuum transfer to provide 13.9 g of 3-[1,1-bis(trifluoromethyl)-2,2,2-trifluoroethoxy]prop-1-ene collected at 0° C. as a colourless liquid; molecular formula $C_7H_5F_9O$ (MW=276.1); MS (m/e$^±$): 276.1; $^1$H NMR (in CDCl$_3$): δ 4.51 (d, J=5.3 Hz, 2H), 5.29 (dtd, J$_1$=10.8 Hz, J$_2$=1.3 Hz, J$_3$=1.3 Hz, 1H), 5.38 (dtd, J$_1$=17.2 Hz, J$_2$=1.5 Hz, J$_3$=1.5 Hz, 1H), 5.90 (ddt, J$_1$=16.0 Hz, J$_2$=10.0 Hz, J$_3$=6.0 Hz, 1H); $^{19}$F NMR (in CDCl$_3$): −73.2 ppm; $^{13}$C NMR (in CDCl$_3$): 70.5, 80.1, 119.0, 120.7, and 131.6 ppm; IR (neat): 3098 (w), 3032 (vw), 2997 (w), 2970 (w), 2912 (w), 1652 (vw), 1469 (w), 1430 (m), 1376 (m), 1275 (vs), 1159 (s), 1089 (w), 1019 (s), 973 (s), 937 (m), 734 (s), 727 (s). 3-[1,1-bis(trifluoromethyl)-2,2,2-trifluoroethoxy]prop-1-ene is a colourless liquid n$_D$=1.3055 @ 25° C.; ρ=1.5992 @ 25° C.; b.p. 78° C. under atmospheric pressure.

3-[1,1-bis(trifluoromethyl)-2,2,2-trifluoroethoxy]prop-1-yne (II) was prepared by adding 1.3 mL (17.8 mmol) propargyl chloride to a stirred solution of 1.1 equivalent or 5.1 g (19.6 mmol) of sodium nonafluoro-tert-butoxide in 5 mL of N,Ndimethylformamide at room temperature and then by heating at 90° C. After 16 hours the addition of 2 mL water to the reaction mixture resulted in the formation of two liquid phases, among which the lower fluorous phase was separated. The fluorous phase was washed with 10 mL of distilled water 3-times. The reaction mixture was purified by distillation at atmospheric pressure. The desired product, 2.74 g of 3-[1,1-bis(trifluoromethyl)-2,2,2-trifluoroethoxy]prop-1-yne was collected at 63° C. as a colourless liquid: (56% yield); MS (m/e+): 274; $^1$H NMR (in d$_6$-DMSO): 54.69 (d, J=2.4 Hz, 2H), 3.36 (t, J=2.4 Hz, 1H); $^{19}$F NMR (in d$_6$-DMSO): −75.4 ppm; $^{13}$C NMR (in d$_6$-DMSO): 58.2, 76.0, 78.9, 79.5 ($^2J_{C-F}$=30 Hz), 120.2 ppm ($^1J_{C-F}$=291 Hz). IR (Neat): 3317 (s), 2965 (m), 2140 (m), 1463 (m), 1276 (vs), 1153 (s), 1026 (s), 972 (s), 727 (s). 3-[1,1-Bis(trifluoromethyl)-2,2,2-trifluoroethoxy]prop-1-yne is a colourless liquid with a density of 1.4452 g/mL at 22° C., and a boiling point of 63° C. under atmospheric pressure.

In general terms, compound I may be prepared by reacting an allyl halide with a metal salt of nonafluoro-tert-butoxide, or with nonafluoro-tert-butyl alcohol in the presence of a base. Compound II may be prepared by reacting a propargyl halide with a metal salt of nonafluoro-tert-butoxide, or with nonafluoro-tert-butyl alcohol in the presence of a base. Preferred metal salts include silver salts, calcium salts, magnesium salts and alkali metal salts. Preferred alkali metal salts include lithium, potassium, sodium and rubidium salts. Bases include solid alkali metal hydroxides in the presence of phase transfer catalysts. The reaction may be carried out in an inert solvent. Preferred solvents would be water soluble, as that facilitates separation of the product. The reaction may be conveniently carried out at temperatures between 20° and 100° C.

The compounds I and II are useful in preparing polymers that have advantageous properties. For example, homopolymers of perfluoro-t-butoxyallyl ether may exhibit high fluorous solubility and partition while at the same time exhibiting decreased toxicity and bioaccumulation. Copolymers of perfluoro-t-butoxyallyl ether may exhibit similar advantages. Monomers suitable for making copolymers with compounds I and II include ethylene, propylene, styrene and vinyl chloride. Similarly, homopolymers and copolymers of perfluoro-t-butoxypropargyl ether are expected to be conductors of electricity but with an oil and water resistant surface.

Homopolymers and copolymers of perfluoro-t-butoxyallyl ether can be made from the corresponding monomer by methods well-known in the art for polymerizing allyl ethers, and particularly for polymerizing electron-withdrawing monomers. For example, the laboratory of Kyoko Nozaki has provided homogeneous organometallic catalysts for polar monomers ["Synthesis of Functional Polyolefins Using Cationic Bisphosphine Monoxide-Palladium Complexes", Carrow and Nozaki, *J. Am. Chem. Soc.*, 2012, 134 (21), pp 8802-8805]. Further, U.S. Pat. No. 5,886,115 describes the direct cationic polymerization of allyl ethers, whereas Venkatesh et al [J Polym Sci Part A: Polym Chem 42: 3271-3284, 2004] describe copolymerizations with acrylates. Similarly, homopolymers and copolymers of perfluoro-t-butoxypropargyl ether can be made from the corresponding monomer by methods well-known in the art for polymerizing propargyl ethers. For example, Balcar et al. [Polymer 39, 4443-4447 (1998)] describes homopolymerization of propargyl ethers in the presence of molybdenum and tungsten-based catalysts, and Tomita et al. [J Polym Sci Part A: Polym Chem 34: 1853-1856, 1996] describes free-radical initiated homopolymerization of propargyl ethers in the presence of potassium t-butoxide. Propargyl ethers are particularly desirable for "Click" chemistry-based construction of polymers. Golas et al. [Austral. J. Chem. 60, 400-404 (2007)] describes block copolymers prepared from a diazido-terminated polystyrene-b-poly(ethylene oxide)-b-polystyrene ABA block copolymer coupled with propargyl ether in the presence of a CuBr/PMDETA catalyst. Click coupling of propargyl ether was also demonstrated with another diazido-terminated triblock copolymer, poly(butyl acrylate)-b-poly(methyl methacrylate)-b-poly(butyl acrylate), and a diazido-terminated pentablock copolymer; poly-styrene-b-poly(butyl acrylate)-b-poly(methyl methacrylate)-b-poly(butyl acrylate)-b-polystyrene.

Polymers prepared by these methods contain repeating units of of formula III or IV:

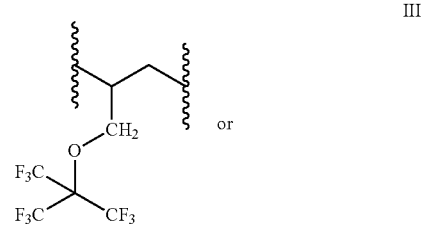

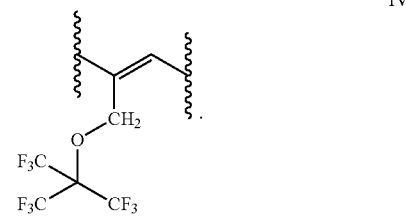

The invention claimed is:
1. A compound of formula II:

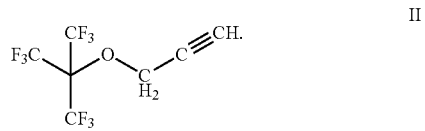

2. A process for preparing a compound of formula II according to claim 1 comprising reacting a propargyl halide with a salt of nonafluoro-tert-butoxide.

3. A process according to claim 2 comprising reacting a propargyl halide with an alkali metal salt of nonafluoro-tert-butoxide.

4. A process for preparing a compound of formula II according to claim 1 comprising reacting a propargyl halide with nonafluoro-tert-butyl alcohol in the presence of a base.

5. A process according to claim 4 comprising reacting a propargyl halide with an alkali metal salt of nonafluoro-tert-butoxide.

* * * * *